(12) United States Patent
Helquist et al.

(10) Patent No.: US 7,235,688 B1
(45) Date of Patent: Jun. 26, 2007

(54) PROCESS FOR PREPARING HISTONE DEACETYLASE INHIBITORS AND INTERMEDIATES THEREOF

(75) Inventors: Paul Helquist, Granger, IN (US); Joakim Löfstedt, South Bend, IN (US)

(73) Assignee: University of Notre Dame Du Lac, Notre Dame, IN (US)

( * ) Notice: Subject to any disclaimer, the term of this patent is extended or adjusted under 35 U.S.C. 154(b) by 0 days.

(21) Appl. No.: 11/108,858

(22) Filed: Apr. 19, 2005

Related U.S. Application Data

(60) Provisional application No. 60/656,532, filed on Feb. 28, 2005, provisional application No. 60/624,524, filed on Nov. 4, 2004, provisional application No. 60/624,523, filed on Nov. 4, 2004.

(51) Int. Cl.
*C07C 229/00* (2006.01)

(52) U.S. Cl. .................. 562/452; 556/413; 556/423; 562/459

(58) Field of Classification Search .................. 562/452; 548/230
See application file for complete search history.

(56) References Cited

U.S. PATENT DOCUMENTS

| | | | |
|---|---|---|---|
| 3,662,031 | A | 5/1972 | Moffatt et al. |
| 4,400,509 | A | 8/1983 | Bruynes et al. |
| 4,549,030 | A | 10/1985 | Pearlman |
| 4,946,999 | A | 8/1990 | Koseki et al. |
| 5,235,057 | A | 8/1993 | Kleemann et al. |
| 5,493,038 | A | 2/1996 | Hall et al. |
| 5,852,198 | A | 12/1998 | Xu et al. |
| 6,133,409 | A | 10/2000 | Salvino et al. |
| 6,326,176 | B1 | 12/2001 | Barbas et al. |
| 6,392,010 | B1 | 5/2002 | Salvino et al. |
| 6,399,627 | B1 | 6/2002 | Song et al. |

(Continued)

FOREIGN PATENT DOCUMENTS

| | | |
|---|---|---|
| JP | 60-149520 | 8/1985 |

(Continued)

OTHER PUBLICATIONS

Wang et al., "QSAR Studies of PC-3 Cell Line Inhibition Activity of TSA and SAHA-Like Hydroxamic Acids," *Bioorg. & Med. Chem Lett.*, 14 (2004): pp. 707-711.

Wang et al., "On the Function of the 14 A Long Internal Cavity of Histone Deacetylase-Like Protein: Implications for the Design of Histone Deacetylase Inhibitors," *J. Med. Chem.*, 47 (2004): pp. 3409-3417.

M. Drew et al., "Selective Cyclizations of Unsaturated Esters Derived from 2,3-O-Isopropylidene-D-Ribose," *J. Chem. Soc. Perkin Trans.*, 1 (1988): pp. 433-437.

S. Hosokawa et al, "The First Total Synthesis of Trichostatin D," *Tetrahedron Lett.*, 46 (2005): pp. 333-337.

(Continued)

*Primary Examiner*—Kamal A. Saeed
*Assistant Examiner*—Yong Chu
(74) *Attorney, Agent, or Firm*—Schwabe, Williamson & Wyatt, P.C.

(57) ABSTRACT

A process for preparing unsaturated esters useful as intermediates for HDAC inhibitors, by reacting an aldehyde or ketone having the following formula I:

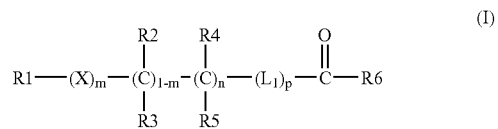

wherein $R_1$ is an aromatic group or a combined aliphatic and aromatic group; X is —O—, —S—, —COO—, —OOC—, —CONR$_7$—, or —R$_7$NCO—; $L_1$ an aliphatic linking group, an aromatic linking group, or a combined aliphatic and aromatic linking group; $R_2$ and $R_3$ are each independently hydrogen, a hydroxy group, an alkoxy group, an amino group, a carboxyl group, an amide group, an ester group, a carbamate group, an aliphatic group, an aromatic group, a combined aliphatic and aromatic group, $R_2$ and $R_3$ together are =O, or one of $R_2$ and $R_3$ form a double bond with one of $R_4$ and $R_5$; $R_4$ and $R_5$ are each independently hydrogen, a hydroxy group, an alkoxy group, an amino group, a carboxy group, an amide group, an ester group, a carbamate group, an aliphatic group, an aromatic group, a combined aliphatic and aromatic group, or one of $R_4$ and $R_5$ form a double bond with one of $R_2$ and $R_3$; $R_6$ is hydrogen, an aliphatic group, an aromatic group, or a combined aliphatic and aromatic group; $R_7$ is hydrogen, an aliphatic group, an aromatic group, or a combined aliphatic and aromatic group; m is 0 or 1; n is 0 or 1; and p is 0 or 1; with an ester having the following formula II:

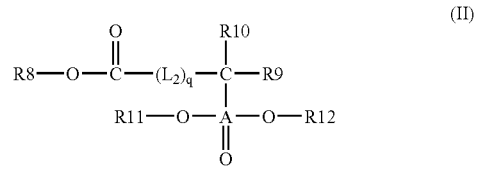

wherein $R_8$ is an aliphatic group, an aromatic group, or a combined aliphatic and aromatic group; $R_9$ and $R_{10}$ each independently hydrogen, an aliphatic group, an aromatic group, a combined aliphatic and aromatic group, or one of $R_9$ and $R_{10}$ form a double bond with $L_2$; $R_{11}$ and $R_{12}$ are each an aliphatic group, an aromatic group, or a combined aliphatic and aromatic group; $L_2$ is an aliphatic linking group, an aromatic linking group, or a combined aliphatic and aromatic linking group; A is P or As; and p is 0 or 1.

13 Claims, 3 Drawing Sheets

U.S. PATENT DOCUMENTS

| | | |
|---|---|---|
| 6,432,981 B1 | 8/2002 | Finke et al. |
| 6,441,186 B1 | 8/2002 | Nicolaou et al. |
| 6,541,661 B1 | 4/2003 | Delorme et al. |
| 6,545,049 B1 | 4/2003 | Cana-Koch et al. |
| 6,552,065 B2 | 4/2003 | Remiszewski et al. |
| 6,562,851 B2 | 5/2003 | Clark et al. |
| 6,562,995 B1 | 5/2003 | Lan-Hargest et al. |
| 6,589,766 B1 | 7/2003 | Barbas et al. |
| 6,593,354 B2 | 7/2003 | Clark et al. |
| 6,593,493 B1 | 7/2003 | Ardecky et al. |
| 6,596,758 B1 | 7/2003 | Brunet et al. |
| 6,620,832 B2 | 9/2003 | Eastwood |
| 6,624,167 B1 | 9/2003 | Clark et al. |
| 6,693,109 B2 | 2/2004 | Fisher et al. |
| 6,706,738 B2 | 3/2004 | Clark et al. |
| 6,759,555 B2 | 7/2004 | Mutti et al. |
| 6,777,217 B1 | 8/2004 | Schreiber et al. |
| 6,777,406 B2 | 8/2004 | Fevig et al. |
| 6,825,185 B2 | 11/2004 | Khanapure et al. |
| 6,833,384 B2 | 12/2004 | Remiszewski et al. |
| 2002/0115826 A1 | 8/2002 | Delorme et al. |
| 2003/0148970 A1 | 8/2003 | Besterman et al. |
| 2003/0152557 A1 | 8/2003 | Besterman et al. |
| 2004/0002506 A1 | 1/2004 | Breslow et al. |
| 2004/0006056 A1 | 1/2004 | Harris et al. |
| 2004/0024067 A1 | 2/2004 | Remiszewski et al. |
| 2004/0127432 A1 | 7/2004 | Nicolaou et al. |
| 2004/0152723 A1 | 8/2004 | Clark et al. |
| 2004/0254145 A1 | 12/2004 | Magnani et al. |
| 2004/0267040 A1 | 12/2004 | Harris et al. |

FOREIGN PATENT DOCUMENTS

| | | |
|---|---|---|
| JP | 61-176523 | 8/1986 |
| JP | 1-224381 | 9/1989 |
| JP | 2-017142 | 1/1990 |
| JP | 3-215449 | 9/1991 |
| JP | 7-206670 | 8/1995 |
| WO | WO 97/36909 | 10/1997 |
| WO | WO 01/18171 | 8/2000 |
| WO | WO 03/084919 | 4/2003 |
| WO | WO 03/097653 | 5/2003 |
| WO | WO 2004/052823 | 11/2003 |
| WO | WO 2004/048323 | 12/2003 |

OTHER PUBLICATIONS

"Horner-Wadsworth-Emmons olefination," at http://orgchem.chem.uconn.edu/namereact/horner.html.

"Olefination of an Aldehyde: Horner Wadsworth Emmons Mechanism," at http://www.umich.edu/~chemh215/WORTHML/SSG1/1.2/mechanism.htm, paper included.

"Suzuki-Type Couplings," http://www.organic-chemistry.org/highlights/2004/15October.shtm. Oct. 15, 2004.

SK-692

SK-658

SK-691

PROCESS FOR PREPARING HISTONE DEACETYLASE INHIBITORS AND INTERMEDIATES THEREOF

CROSS-REFERENCE TO RELATED APPLICATIONS

This application makes reference to and claims the benefit of co-pending U.S. Provisional Patent Applications No. 60/624,523, filed Nov. 4, 2004, No. 60/624,524, filed Nov. 4, 2004, and No. 60/656,532, filed Feb. 28, 2005. The entire disclosure and contents of the foregoing Provisional Applications are hereby incorporated by reference herein.

BACKGROUND

1. Field of the Invention

The present invention relates generally to a process for preparing histone deacetylase inhibitors, as well as intermediates thereof.

2. Related Art

Histone deacetylase (HDAC) inhibitors are promising compounds for the development of anti-cancer, as well as anti-malarial drugs. HDAC inhibitors include simple fatty acid compounds such as sodium butyrate, phenylbutyrate, and valproic acid, up to more complex cyclic tetrapeptide antibiotics such as apidicin, trapoxin B and depsipeptide. Most of the known HDAC inhibitors are hydroxamic acids or derivatives thereof such as trichostatin A (TSA) and suberoylanilide hydroxamic acid (SAHA). See Wang et al., "QSAR Studies of PC-3 Cell Line Inhibition Activity of TSA and SAHA-Like Hydroxamic Acids," *Bioorg. & Med. Chem. Lett.*, 14 (2004): pp. 707–11.

The most potent HDAC inhibitor discovered so far is TSA. TSA is a relatively rare natural product that was originally isolated from *Streptomyces hygroscopicus*. See Tsji et al., "New Antifungal Antibiotic, Trichostatin," *J. Antibiot.*, 29 (1976): pp. 1–6; Yoshida et al., "Trichostatin-A and Trapoxin—Novel Chemical Probes for the Role of Histone Acetylation in Chromatin Structure and Function," *BioEssay*, 17 (1995): pp. 423–30. TSA has been previously synthesized as both racemic and enantiomerically pure forms. See Fleming et al., "The Total Synthesis of (+/−)-Trichostatin-A—Some Observations on the Acylation and Alkylation of Silyl Enol Ethers, Silyl Dienol Ethers and a Silyl Trienol Ether," *Tetrahedron*, 39 (1983): pp. 841–46; K. Mori et al, "Synthetic Microbial Chemistry: Synthesis of Trichostatin-A, a Potent Differentiation Inducer of Friend Leukemic-Cells, and its Antipode," *Tetrahedron*, 44 (1988): pp. 6013–20. However, these prior syntheses for TSA require a significant number synthesis steps (e.g., upwards of 20 synthesis steps), and are therefore relatively inefficient and impractical to economically produce TSA. Because these prior syntheses for producing TSA are inefficient, impractical and costly, others have searched for alternative HDAC inhibitors. Indeed, because of the difficulty in synthesizing TSA and the relatively high cost of TSA (e.g., ~$100/mg.), TSA is used today mainly as a reference substance in the research for new HDAC inhibitors.

Accordingly, it would be desirable to provide a process for synthesizing TSA, including intermediates thereof, as well as other HDAC inhibitors, that: (1) requires fewer synthesis steps; (2) is more practical, (3) is more efficient; (4) is less expensive; and/or (5) has the processing flexibility to prepare a wide variety of HDAC inhibitors, and their respective intermediates, by using the same or similar processing steps.

SUMMARY

According to a first broad aspect of the present invention, there is provided a process for preparing an unsaturated ester comprising the following steps:

(a) providing an aldehyde or ketone having the following formula I:

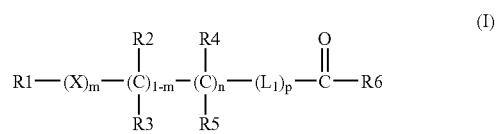

wherein $R_1$ is an aromatic group or a combined aliphatic and aromatic group; X is —O—, —S—, —COO—, —OOC—, —CONR$_7$—, or —R$_7$NCO—; $L_1$ an aliphatic linking group, an aromatic linking group, or a combined aliphatic and aromatic linking group; $R_2$ and $R_3$ are each independently hydrogen, a hydroxy group, an alkoxy group, an amino group, a carboxy group, an amide group, an ester group, a carbamate group, an aliphatic group, an aromatic group, a combined aliphatic and aromatic group, $R_2$ and $R_3$ together are =O, or one of $R_2$ and $R_3$ form a double bond with one of $R_4$ and $R_5$; $R_4$ and $R_5$ are each independently hydrogen, a hydroxy group, an alkoxy group, an amino group, a carboxy group, an amide group, an ester group, a carbamate group, an aliphatic group, an aromatic group, a combined aliphatic and aromatic group, or one of $R_4$ and $R_5$ form a double bond with one of $R_2$ and $R_3$; $R_6$ is hydrogen, an aliphatic group, an aromatic group, or a combined aliphatic and aromatic group; $R_7$ is hydrogen, an aliphatic group, an aromatic group, or a combined aliphatic and aromatic group; m is 0 or 1; n is 0 or 1; and p is 0 or 1; m, n, p, and $L_1$ being selected so that the number of carbon atoms directly in the carbon chain between the $R_1$ and $R_6$ groups is at least 2;

(b) providing an ester having the following formula II:

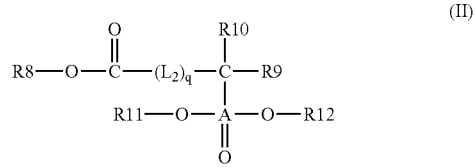

wherein $R_8$ is an aliphatic group, an aromatic group, or a combined aliphatic and aromatic group; $R_9$ and $R_{10}$ are each independently hydrogen, an aliphatic group, an aromatic group, a combined aliphatic and aromatic group, or one of $R_9$ and $R_{10}$ form a double bond with $L_2$; $R_{11}$ and $R_{12}$ are each independently an aliphatic group, an aromatic group, or a combined aliphatic and aromatic group; $L_2$ is an aliphatic linking group, an aromatic linking group, or a combined aliphatic and aromatic linking group; A is P or As; and q is 0 or 1; q and $L_2$ being selected so that the number of carbon atoms directly in the carbon chain between the $R_8$ and $R_9$ groups is at least 2; and (c) reacting the ester of formula II with the aldehyde or ketone of formula I to form an unsaturated ester having the following formula III:

$$R1-(X)_m-\underset{R3}{\overset{R2}{\underset{|}{C}}}_{1-m}-\underset{R5}{\overset{R4}{\underset{|}{C}}}_n-(L_1)_p-\overset{R6}{\underset{|}{C}}=\underset{R10}{\overset{}{C}}-(L_2)_q-\overset{O}{\overset{\|}{C}}-O-R8; \quad \text{(III)}$$

wherein m, n, p, q, $L_1$ and $L_2$ are selected so that the number of carbon atoms directly in the carbon chain between the $R_1$ and $R_8$ groups is at least 4.

According to a second broad aspect of the invention, there is provided a process for preparing an ester derivative comprising the following steps:

(a) preparing an aldehyde or ketone having the following formula I:

$$R1-(X)_m-\underset{R3}{\overset{R2}{\underset{|}{C}}}_{1-m}-\underset{R5}{\overset{R4}{\underset{|}{C}}}_n-(L_1)_p-\overset{O}{\overset{\|}{C}}-R6 \quad \text{(I)}$$

wherein $R_1$, $R_2$, $R_3$, $R_4$, $R_5$, $R_6$, X, $L_1$, m, n and p are defined as before;

(b) providing an ester having the following formula II:

$$R8-O-\overset{O}{\overset{\|}{C}}-(L_2)_q-\overset{R10}{\underset{R11-O-\underset{\overset{\|}{O}}{A}-O-R12}{\overset{|}{C}}}-R9 \quad \text{(II)}$$

wherein $R_8$, $R_9$, $R_{10}$, $R_{11}$, $R_{12}$, A, $L_2$, and q are defined as before;

(c) reacting the ester of formula II with the aldehyde or ketone of formula I to form an unsaturated ester having the following formula III:

$$R1-(X)_m-\underset{R3}{\overset{R2}{\underset{|}{C}}}_{1-m}-\underset{R5}{\overset{R4}{\underset{|}{C}}}_n-(L_1)_p-\overset{R6}{\underset{|}{C}}=\underset{R10}{\overset{}{C}}-(L_2)_q-\overset{O}{\overset{\|}{C}}-O-R8 \quad \text{(III)}$$

wherein m, n, p, q, $L_1$ and $L_2$ are selected so that the number of carbon atoms directly in the carbon chain between the $R_1$ and $R_8$ groups is at least 4; and (d) converting the unsaturated ester of formula III to a derivative having the following formula IV:

$$R1-(X)_m-\underset{R3}{\overset{R2}{\underset{|}{C}}}_{1-m}-\underset{R5}{\overset{R4}{\underset{|}{C}}}_n-(L_1)_p-\overset{R6}{\underset{|}{C}}\text{---}\underset{R10}{\overset{}{C}}-(L_2)_q-\overset{Y_1}{\overset{\|}{C}}\text{---}Z_1 \quad \text{(IV)}$$

wherein $Y_1$ is =O, =S, =$NR_{13}$, —$R_{13}$ when $Z_1$ is =$NOR_{15}$, or together with $Z_1$ is ≡N; $Z_1$ is —OH, halo, —$R_{13}$, —$NR_{13}R_{14}$, —$NR_{13}OR_{15}$, —$NR_{13}NR_{13}R_{15}$, —$L_3$—$NR_{13}R_{14}$, —$L_3$—$NR_{13}C(=NR_{13})NR_{13}R_{15}$, —$L_3$—$Y_2R_{13}$, —$L_3$—$C(=Y_2)Z_2$, —$L_3$—$PO_3R_{13}R_{15}$, =$NOR_{15}$ when $Y_1$ is —$R_{13}$, or together with $Y_1$ is ≡N, wherein $L_3$ is an aliphatic linking group, an aromatic linking group, or a combined aliphatic and aromatic linking group, $R_{13}$ and $R_{15}$ are each independently hydrogen, an aliphatic group, an aromatic group or a combined aliphatic and aromatic group, $R_{14}$ is hydrogen, a hydroxy group, an aliphatic group, an aromatic group or a combined aliphatic and aromatic group, $Y_2$ is O or S, and $Z_2$ is —$Y_2R_{13}$, —$NR_{13}R_{14}$, or —$NR_{13}NR_{13}R_{15}$.

According to a third broad aspect of the invention, there is provided a process for preparing trichostatic acid or trichostatin A comprising the following steps:

(a) providing an aldehyde having the following formula V:

(V)

(b) providing a unsaturated phosphonate ester having the following formula VI:

(VI)

(c) reacting the aldehyde of formula V with the unsaturated phosphonate ester of formula VI to provide an unsaturated ester having the following formula VII:

(VII)

(d) hydrolyzing the unsaturated ester of formula VII to provide a carboxylic acid having the following formula VIII:

(VIII)

(e) converting the carboxylic acid of formula VIII to trichostatic acid; and (f) optionally converting the trichostatic acid of step (e) to trichostatin A.

Embodiments of the present invention provide an efficient, practical and cost effective process to prepare unsaturated esters of formula III that are useful as intermediates in preparing, for example, HDAC inhibitors, and potentially HDAC inhibitor prodrugs. Certain embodiments of the present invention especially provide a more, efficient, practical and cost effective process to prepare HDAC inhibitors, such as trichostatin A, and especially intermediates such as trichostatic acid, that can be readily converted into trichostatin A or other HDAC inhibitors/prodrugs. The present invention also provides the flexibility to prepare a wide of variety of HDAC inhibitors/prodrugs, and respective intermediates thereof, using the same or similar processing steps. Embodiments of the present invention also generally require fewer processing steps to obtain the desired intermediates and HDAC inhibitors/prodrugs, including trichostatic acid and trichostatin A.

BRIEF DESCRIPTION OF THE DRAWINGS

The invention will be described in conjunction with the accompanying drawings, in which.

DETAILED DESCRIPTION

Figure 1:
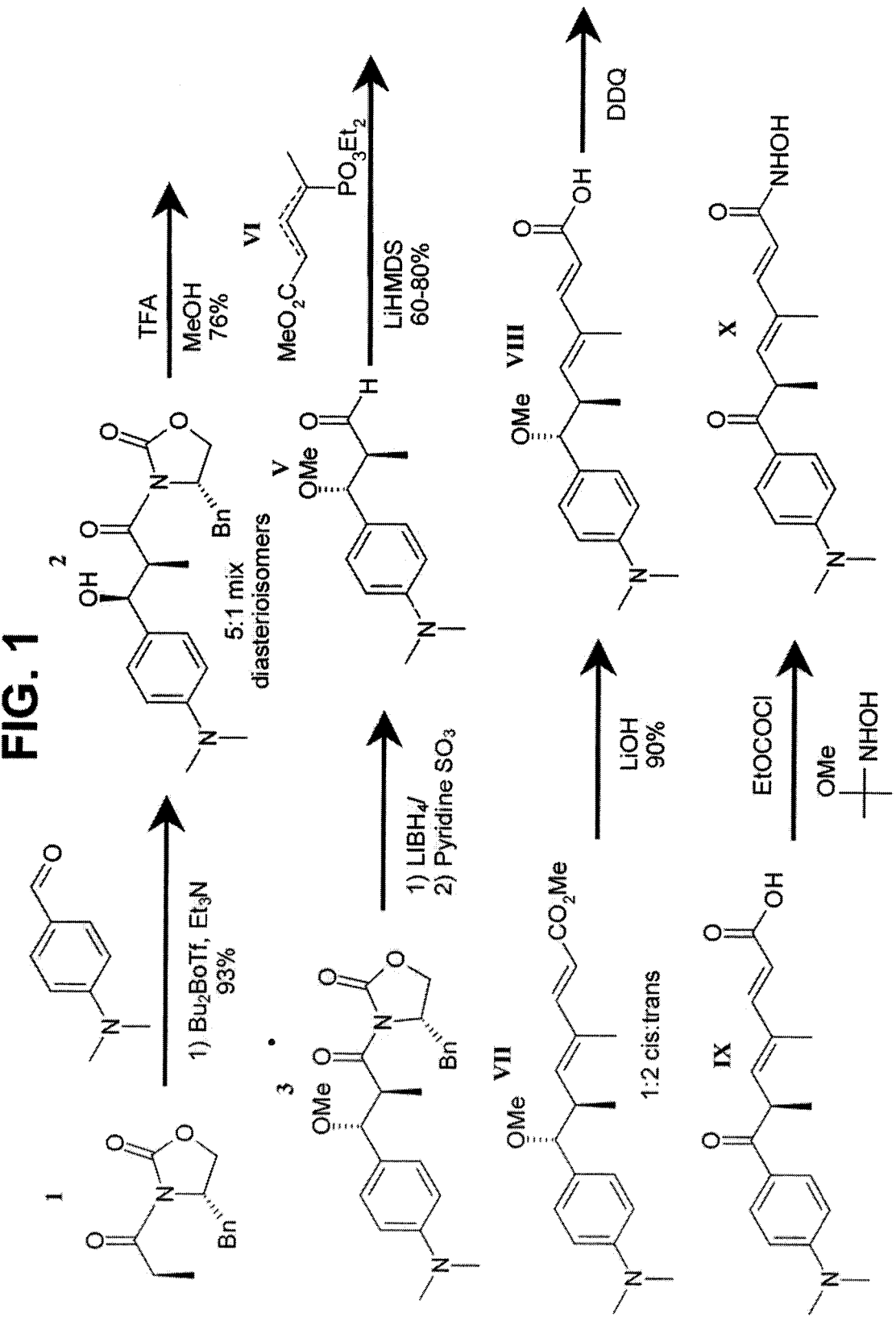
FIG. 1 illustrates Scheme 1 of the process of the present invention for preparing trichostatic acid and trichostatin A.

It is advantageous to define several terms before describing the invention. It should be appreciated that the following definitions are used throughout this application.

Definitions

Where the definition of terms departs from the commonly used meaning of the term, applicant intends to utilize the definitions provided below, unless specifically indicated.

For the purposes of the present invention, the term "aromatic" refers to an unsaturated cyclic arene moiety containing one or more unsaturated cyclic rings (typically 5 and/or 6 atoms per ring) that can be substituted, unsubstituted, or a combination thereof, can be heterocyclic (i.e., including one or more oxygen atoms, nitrogen atoms, sulfur atoms, etc.), nonheterocyclic, or a combination thereof, can have any desired number of carbon atoms, e.g., from 3 to 30 carbon atoms, typically from 3 to 18 carbon atoms, more typically from 3 to 12 carbon atoms, etc. Aromatic moieties suitable herein can include, but are not limited to, substituted or unsubstituted phenyl, naphthyl, biphenyl, binaphthyl, phenanthenryl, anthracenyl, pyridinyl, pyrimidinyl, purinyl, pyrinyl, furanyl, thiophenyl, benzofuranyl, benzothiophenyl, dibenzofuranyl, dibenzothiophenyl, imadazolyl, oxazolyl, thiazolyl, pyrazolinyl, indolyl, pyridazinyl, pyrazinyl, triazolyl, quinolinyl, isoquinolinyl, benzoquinolinyl, phenanthrolinyl (e.g., 1,10-phenanthrolyl), carbazolyl, etc. Suitable substituents can include, but are not limited to, halo (i.e., fluoro, chloro, bromo, iodo), alkyl (e.g., methyl, ethyl, propyl, butyl, etc.) and substituted alkyl (e.g., hydroxymethyl, hydroxyethyl, trifluoromethyl, alkoxymethyl, etc.), amino and substituted amino (e.g., dimethylamino, etc.), hydroxy (e.g., a phenol), carboxy, sulfonate, ester, amide, sulfonamide, carbamate, acyl (i.e., aldehyde or ketone), nitro, etc., or any combination thereof.

For the purposes of the present invention, the term "aliphatic" refers to a carbon-containing moiety other than an aromatic moiety. Aliphatic moieties can be straight chain, branched chain, cyclic (cycloaliphatic), or any combination thereof, can be substituted or unsubstituted, can include one or more heteroatoms (e.g., oxygen atoms, nitrogen atoms, sulfur atoms, etc.) in the carbon chain (i.e., can be heterocyclic), can be unsaturated (i.e., one, two or more double bonds) or saturated, etc, and can have any desired number of carbon atoms, e.g., from 1 to 30 carbon atoms, typically from 1 to 12 carbon atoms, more typically from 1 to 6 carbon atoms, etc. Aliphatic moieties suitable herein can include, but are not limited to, substituted or unsubstituted alkyl, alkenyl, alkadienyl, alkynyl, cycloalkyl, cycloalkenyl, etc. Suitable substituents can include, but are not limited to, halo (i.e., fluoro, chloro, bromo, iodo), alkyl (e.g., methyl, ethyl, propyl, butyl, etc.) and substituted alkyl (e.g., hydroxylmethyl, hydroxyethyl, trifluoromethyl, alkoxymethyl, etc.), hydroxy, amino and substituted amino (e.g., dimethylamino, etc.), carboxy, sulfonate, ester, amide, sulfonamide, carbamate, acyl (i.e., aldehyde or keto), etc., or any combination thereof.

For the purposes of the present invention, the term "combined aliphatic and aromatic" refers to a moiety comprising one or more aliphatic moieties and one or more aromatic moieties. Suitable combined aliphatic and aromatic moieties can include, but are not limited to, unsubstituted and substituted benzyl, phenylethyl, phenylpropyl, phenylbutyl, tribenzylmethyl, tribenzylethyl, phenylalkenyl, phenylalkadienyl, phenylalkatrienyl, phenylalkynl, etc., or any combination thereof.

For the purposes of the present invention, the formulas used in the specification, in the claims or in the drawings can represent a single compound, a mixture of compounds, a single enantiomer or a mixture of enantiomers (i.e., a racemic mixture), a single diastereomer or a mixture of diastereomers, etc., unless otherwise specified.

For the purposes of the present invention, the bond symbol "$=\!=\!=$" used in the formulas in the specification, in the claims or in the drawing figures represents a bond that can be either a single or double bond, unless otherwise specified.

For the purposes of the present invention, the following abbreviations are used in the specification, in the claims or in the drawing figures: "Bn" refers to benzyl; "Me" refers to methyl; "Et" refers to ethyl; "$Bu_2BOTf$" refers to di-n-butyl borontrifluoromethanesulfonate; "$Et_3N$" refers to triethylamine; "TFA" refers to trifluoroacetic acid; "MeOH" refers to methanol; "$LiBH_4$" refers to lithium borohydride; "$SO_3$" refers to sulfur trioxide; "LiHMDS" refers to lithium hexamethyldisilazide; "LiOH" refers to lithium hydroxide; "EtOCOCl" refers to ethyl chloroformate.

For the purposes of the present invention, the term "HDAC" is used to refer to histone deacetylases. Histone deacetylases are enzymes that typically regulate the hydrolysis of the ε-acetylated lysine in histones. See Wang et al., "QSAR Studies of PC-3 Cell Line Inhibition Activity of TSA and SAHA-Like Hydroxamic Acids," *Bioorg, & Med. Chem. Lett.*, 14 (2004): pp. 707–11, which is incorporated by reference.

For the purposes of the present invention, the term "HDAC inhibitor" refers to those compounds, compositions, molecules, etc., that partially or completely inhibit the activity of histone deacetylases, including prodrugs.

For the purposes of the present invention, the term "prodrug" refers to a compound, molecule, etc., that is converted by metabolic processes in the body into an active form of a drug, e.g., an HDAC inhibitor.

For the purposes of the present invention, the term "intermediate" typically refers to a compound or compounds that are prepared by a process or step of the present invention that is a precursor of, and can be subsequently used, directly or indirectly, to prepare an end product. For example, intermediates can be used to prepare other intermediates that are then used to prepare an end product. In certain instances, intermediates that are prepared by the process of the present invention can also function as prodrugs.

For the purposes of the present invention, the term "end product" refers to the product obtained at the end or completion of the process, and is typically the product that is ultimately desired from the process.

For the purposes of the present invention, the term "process" refers to one or more steps used to prepare one or more compounds, including one or more intermediates, as well as one or more end products.

For the purposes of the present invention, the term "scheme" refers to a synthesis design, framework, etc., comprising two or more processing steps for preparing specific intermediates and/or end products.

Description

Aspects of the present invention are generally directed to processes for preparing certain unsaturated esters useful as intermediates in preparing various end products, and in particular HDAC inhibitors and/or HDAC inhibitor prodrugs, including trichostatic acid and trichostatin A. The process of embodiments of the present invention can encompass the processing step or steps for preparing the unsaturated esters, including any processing steps required for synthesizing, preparing or providing reactants used in preparing these unsaturated esters, as well as any subsequent processing steps for converting these unsaturated esters into other compounds, including conversion into intermediates used in preparing HDAC inhibitors, conversion into HDAC inhibitors, and/or conversion into HDAC inhibitor prodrugs.

The unsaturated esters that are prepared by certain processes of the present invention have the following formula III:

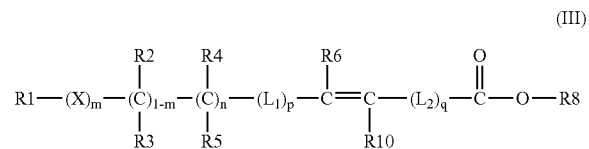

wherein $R_1$, $R_2$, $R_3$, $R_4$, $R_5$, $R_6$, $R_8$, $R_{10}$, X, $L_1$ and $L_2$ are defined hereafter. For example, in the unsaturated ester of formula III that is typically the intermediate used in preparing trichostatic acid (as well as trichostatin A), $R_1$ is a 4-dimethylaminophenyl group, m is 0, n is 1, p is 0, $R_2$ is an alkoxy group having from 1 to 4 carbon atoms, and is typically methoxy, $R_3$ is hydrogen, $R_4$ is hydrogen, $R_5$ is methyl, $R_6$ is hydrogen, $R_8$ is typically an alkyl group having from 1 to 4 carbon atoms, and more typically methyl, q is 1, $L_2$ is —$CH_2$═$CH_2$—, $R_{10}$ is methyl, as represented, for example, by the unsaturated ester having formula VII shown in Scheme 1 of FIG. 1.

For the unsaturated esters of formula III (e.g., those of formula VII), the m, n, p and q values, as well as the $L_1$ and $L_2$ groups, are selected so that the number of carbon atoms directly in the carbon chain between the $R_1$ and $R_8$ groups is at least 4, typically from 4 to 8, more typically from 7 to 8. HDAC inhibitors and intermediates thereof, such as trichostatic acid and trichostatin A, prepared from such unsaturated esters of formula III (e.g., of those formula VII) have at least 4 carbon atoms in this carbon chain, typically from 4 to 8 carbon atoms, and more typically from 7 to 8 carbon atoms.

One of the reactants used in preparing the unsaturated esters of formula III is an aldehyde or ketone having the following formula I:

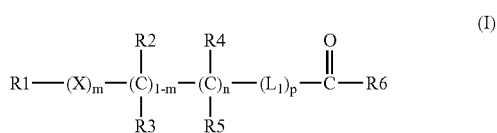

wherein $R_1$ is an aromatic group or a combined aliphatic and aromatic group; X is —O—, —S—, —COO—, —OOC—, —CONR$_7$—, or —$R_7$NCO—; $L_1$ an aliphatic linking group, an aromatic linking group, or a combined aliphatic and aromatic linking group; $R_2$ and $R_3$ are each independently (i.e., same or different) hydrogen, a hydroxy group, an alkoxy group, an amino group, a carboxy group, an amide group (e.g., —OCNHR$_{16}$, wherein $R_{16}$ is, for example, an aromatic group or a combined aromatic and aliphatic group), an ester group, a carbamate group (e.g., —NHCOOR$_{16}$, wherein $R_{16}$ is, for example, an aromatic group or a combined aromatic and aliphatic group), an aliphatic group, an aromatic group, a combined aliphatic and aromatic group, $R_2$ and $R_3$ together are ═O, or one of $R_2$ and $R_3$ form a double bond with one of $R_4$ and $R_5$; $R_4$ and $R_5$ are each independently (i.e., same or different) hydrogen, a hydroxy group, an alkoxy group, an amino group, a carboxy group, an amide group, an ester group, a carbamate group, an aliphatic group, an aromatic group, a combined aliphatic and aromatic group, or one of $R_4$ and $R_5$ form a double bond with one of $R_2$ and $R_3$; $R_6$ is hydrogen, an aliphatic group, an aromatic group, or a combined aliphatic and aromatic group; $R_7$ is hydrogen, an aliphatic group, an aromatic group, or a combined aliphatic and aromatic group; m is 0 or 1; n is 0 or 1; and p is 0 or 1, $R_1$, $R_2$, $R_3$, $R_4$, $R_5$, $R_6$, X, $L_1$, m, n and p are typically selected depending on the unsaturated ester of formula III that is desired, to protect other potentially reactive sites on the aldehyde/ketone of formula I, etc. For example, when the $R_1$ group is a substituted aromatic group, the substituent is typically an electron donating substituent such as halo (e.g., bromo, etc.), amino or substituted amino (e.g., dimethylamino, etc.). The values for m, n, and p, as well as the $L_1$ group, are also selected so that the number of carbon atoms directly in the carbon chain between the $R_1$ and $R_6$ groups is at least 2, typically from 2 to 5, more typically from 3 to 4. For example, in the aldehyde of formula I that is typically used to prepare the unsaturated ester of formula VII, $R_1$ is a 4-dimethylaminophenyl group, m is 0, n is 1, p is 0, $R_2$ is an alkoxy group having from 1 to 4 carbon atoms and is typically methoxy, $R_3$ is hydrogen, $R_4$ is hydrogen, $R_5$ is methyl and $R_6$ is hydrogen, as represented, for example, by the aldehyde having formula V shown in Scheme 1 of FIG. 1.

Another reactant used in preparing the unsaturated esters of formula III is an ester having the following formula II:

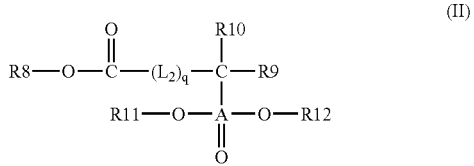

(II)

wherein $R_8$ is an aliphatic group, an aromatic group, or a combined aliphatic and aromatic group; $R_9$ and $R_{10}$ are each independently (i.e., same or different) hydrogen, an aliphatic group, an aromatic group, a combined aliphatic and aromatic group, or one of $R_9$ and $R_{10}$ form a double bond with $L_2$; $R_{11}$ and $R_{12}$ are each independently (i.e., same or different) an aliphatic group, an aromatic group, or a combined aliphatic and aromatic group; $L_2$ is an aliphatic linking group, an aromatic linking group, or a combined aliphatic and aromatic linking group; A is P or As; and p is 0 or 1. Typically, A is P, i.e., the esters of formula II are typically phosphonate esters, and $R_{11}$ and $R_{12}$ are each typically an alkyl group having from 1 to 4 carbon atoms such as ethyl or methyl. $R_8$, $R_9$, $R_{10}$, $R_{11}$, $R_{12}$, A, $L_2$, and q are typically selected depending on the unsaturated ester of formula III that is desired, to favor or promote the desired reaction with the aldehyde/ketone of formula I, etc. The value for q and the $L_2$ group are also selected so that the number of carbon atoms directly in the carbon chain between the $R_8$ and $R_9$ groups is at least 2, typically from 2 to 5, and more typically from 3 to 4. For example, in the ester of formula II that is typically used to prepare the unsaturated ester of formula VIII, $R_8$ is typically an alkyl group having from 1 to 4 carbon atoms such as methyl, q is 1, $L_2$ typically has at least one double bond (e.g., —$CH_2$=$CH_2$—) and/or forms a double bond with one of $R_9$ and $R_{10}$, $R_9$ is hydrogen or forms a double bond with $L_2$, $R_{10}$ is a methyl group, A is P, and $R_{11}$ and $R_{12}$ are each typically an alkyl group having from 1 to 4 carbon atoms such as ethyl, as represented, for example, by the unsaturated phosphonate ester having formula VI shown in Scheme 1 of FIG. 1. The unsaturated phosphonate esters such as those of formula VI can be prepared by an Arbuzov reaction using, for example, the respective alkyl halides and trialkyl phosphites as reactants, and typically provide a mixture of unsaturated phosphonate esters (e.g., the 2- and 3-unsaturated phosphonate esters represented in formula VI). See A. Arbuzov et al., *J. Russ Phys. Chem. Soc.*, 46 (1914): p. 295 et. seq., (incorporated by reference herein), for a description of a general approach for providing phosphonate esters of formula III and especially formula VI.

In preparing unsaturated esters of formula III, the ester of formula II is typically reacted with the aldehyde/ketone of formula I under reaction conditions that favor or promote the nucleophilic addition of the carbon adjacent to the A group of the ester of formula II, to the carbonyl carbon adjacent to the $R_6$ group of the aldehyde/ketone of formula II, while at the same minimizing other undesired reactions or effects, including preserving desired siereoisomeric configurations. This reaction typically uses a strong base that is weakly nucleophilic, for example, sodium hydride or alkali metal amide bases such as lithium hexamethyldisilazide, lithium di-isopropyl amide, lithium isopropylcyclohexyl amide, lithium dicyclohexylamide, sodium hexamethyldisilazide, potassium hexamethyldisilazide, lithium amide, etc. This strong base is typically initially added to the ester of formula II at relatively low temperatures (e.g., as low as about −80° C.), with the reaction product of the strong base and ester of formula II then being reacted with the aldehyde/ketone of formula I. The reaction between the aldehyde/ketone of formula I and the ester of formula II can be carried out in any compatible solvent including, but not limited to, ethers such as diethyl ether, methyl ethyl ether, t-butylmethylether, etc., cyclic ethers such as tetrahydrofuran (THF), dioxane, tetrahydropyran, etc., diethers such as dimethoxyethane, etc., esters such as methyl acetate, ethyl acetate, etc., aromatic solvents such as toluene, etc., amides such as dimethylformamide (DMF), dimethylacetamide, etc., acetonitrile, dimethylsulfoxide (DMSO), etc. After the addition of the strong base, the condensation reaction between the aldehydes/ketones of formula I and esters of formula II can be carried out at temperatures in the range of typically from about −20° to about 75° C., more typically in the range from about 0° to about 30° C. The rate at which the reaction proceeds can vary depending on such factors as the aldehydes/ketones of formula I and esters of formula II that are reacted, the strong bases that are used, etc., but is typically complete in from about 1 to about 24 hours, more typically in from about 1 to about 12 hours, with yields of the unsaturated ester of formula III typically in the range of from about 40 to about 80%, and more typically in the range of from about 60 to about 80%.

The unsaturated esters of formula III can also be converted into derivatives having the following formula IV:

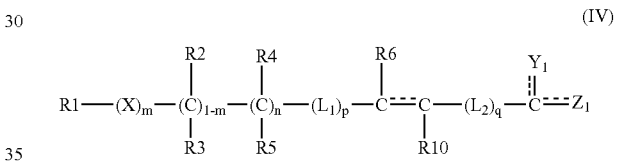

(IV)

wherein $Y_1$ is =O, =S, =$NR_{13}$, —$R_{13}$ when $Z_1$ is =$NOR_{15}$, or together with $Z_1$ is =N; $Z_1$ is —OH, halo (typically chloro), —$R_{13}$, —$NR_{13}R_{14}$, —$NR_{13}OR_{15}$, —$NR_{13}NR_{13}R_{15}$, —$L_3$—$NR_{13}R_{14}$, —$L_3$—$NR_{13}C$(=$NR_{13}$)$NR_{13}R_{15}$, —$L_3$—$Y_2R_{13}$, —$L_3$—C(=$Y_2$)$Z_2$, —$L_3$—$PO_3R_{13}R_{15}$, =$NOR_{15}$ when $Y_1$ is —$R_{13}$, or together with $Y_1$ is =N, wherein $L_3$ is an aliphatic linking group, an aromatic linking group, or a combined aliphatic and aromatic linking group, typically a saturated or unsaturated aliphatic linking group, and more typically —($CH_2$)$_k$—, wherein k is at least 1, and typically is from 1 to 8, more typically from 1 to 6, $R_{13}$ and $R_{15}$ are each independently (i.e., same or different) hydrogen, an aliphatic group (including cyclic or heterocyclic aliphatic groups having heteroatoms such as O, S or N, and typically having from 3 to 6 total atoms in the cyclic ring), an aromatic group or a combined aliphatic and aromatic group, $R_{14}$ is hydrogen, a hydroxy group, an aliphatic group, an aromatic group or a combined aliphatic and aromatic group, $Y_2$ is O or S (typically O), and $Z_2$ is —$Y_2R_{13}$, —$NR_{13}R_{14}$, or —$NR_{13}NR_{13}R_{15}$. $Y_1$ is typically =O, while $Z_1$ is typically a —OH (i.e., a carboxylic acid), —$NR_{13}R_{14}$ wherein $R_{13}$ is typically hydrogen and $R_{14}$ is typically hydroxy (i.e., a hydroxamic acid), or —$CH_2$—$PO_3R_{13}R_{15}$, group, wherein $R_{13}$ and $R_{15}$ are each typically hydrogen or an alkyl group of from 1 to 4 carbon atoms, more typically ethyl or methyl (i.e., a phosphonate).

One such derivative that unsaturated esters of formula III can be relatively easily converted into are the respective carboxylic acids (i.e., wherein $Y_1$ is =O and $Z_1$ is —OH in formula IV) having the following formula XI:

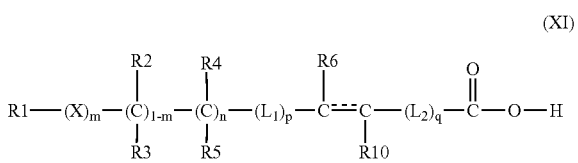

Conversion of the unsaturated esters of formula III into carboxylic acids of formula XI (deesterification) can be achieved by art-recognized hydrolysis reactions, including treatment with a strong base (i.e., saponification) such as lithium hydroxide, sodium hydroxide, potassium hydroxide, etc., to hydrolyze the unsaturated ester of formula III to the respective carboxylic acid of formula XI. For example, as illustrated in Scheme 1 of FIG. 1, the unsaturated ester VII can be hydrolyzed (saponified) by treatment with lithium hydroxide to the respective carboxylic acid VIII.

Carboxylic acids of formula XI can also be converted into various carboxylic derivatives. One such carboxylic acid derivative that can be formed from the carboxylic acid of formula XI is a hydroxamic acid (i.e., wherein $Y_1$ is =O and $Z_1$ is —NHOH in formula IV), as represented by the following formula XII:

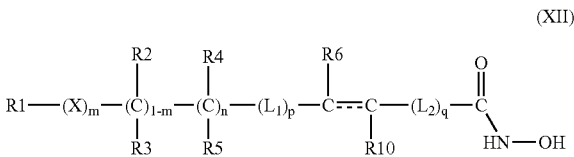

For example, as illustrated in Scheme 1 of FIG. 1, trichostatic acid of formula IX can be reacted (e.g., after activation, for example, by ethyl chloroformate) with a hydroxylamine (e.g., O-(2-methoxy-2-propyl)hydroxylamine) to provide the hydroxamic acid trichostatin A of formula X (i.e., wherein $R_1$ is 4-dimethylaminophenyl, m is 0, $R_2$ and $R_3$ are together =O, $R_4$ is hydrogen, $R_5$ is methyl, p is 0, $R_6$ is methyl, q is 1, and $L_2$ is —CH$_2$=CH$_2$— in formula XII).

To provide phosphonate derivatives of formula IV (i.e., wherein $Y_1$ is =O and $Z_1$ is —CH$_2$—PO$_3$R$_{13}$R$_{15}$), the unsaturated esters of formula III (wherein $R_8$ is typically a methyl group), or the respective acyl chloride (i.e., wherein $R_8$ is chloro) are typically reacted with a metalated phosphonate such as a Li—CH$_2$—PO$_3$R$_{13}$R$_{15}$ (wherein $R_{13}$ and $R_{15}$ are each typically hydrogen or an alkyl group having from 1 to 4 carbon atoms, and more typically an ethyl or methyl group). See F. Orsini et al., *Tetrahedron Lett.*, 43 (2002): p. 7259 et seq. and references cited therein (herein incorporated by reference), for a description of a general approach for providing these phosphonate derivatives.

The unsaturated esters of formula III, as well as the derivatives of formula IV, can also be subjected to one or more other processing steps. These other processing steps can include the removal of protecting groups, the conversion of existing substituent groups (e.g., alkoxy groups, etc.) to other substituent groups (e.g., =O, etc.), conversion of double bonds to single bonds (e.g., by hydrogenation) in the carbon chain directly between the $R_1$ and $Z_1$ groups (e.g., double bond between the carbon atoms having the $R_6$ and $R_{10}$ groups, etc.), and can occur prior to and/or after conversion of the unsaturated esters of formula III to the derivatives of formula IV. For example, as illustrated in Scheme 1 of FIG. 1, the carboxylic acid represented by formula VIII that is obtained after deesterification (e.g., saponification) of the unsaturated ester of formula V is typically oxidized by treatment with a selective oxidizing agent such as 2,3-dichloro-5,6-dicyanobenzoquinone (DDQ) to form trichostatic acid (the respective keto acid wherein $R_2$ and $R_3$ together become =O in formula IV), as represented by formula X in Scheme 1 of FIG. 1.

One group of representative ester derivatives that can be obtained by the process of the present invention are those having either of the following formulas XIII or XIV:

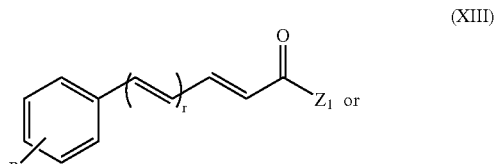

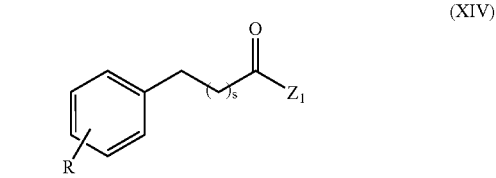

wherein $Z_1$ is defined as before and is typically —NHOH, or —CH$_2$—PO$_3$R$_{13}$R$_{15}$, wherein R$_{13}$ and R$_{15}$ are each typically hydrogen or an alkyl group having from 1 to 4 carbon atoms, more typically ethyl or methyl; r is at least 1 and is typically from 1 to 3, more typically from 1 to 2; s is at least 2, and is typically from 3 to 7, more typically from 5 to 7; and R is either hydrogen or a substituent group, typically an electron donating substituent group such as halo (e.g., bromo, etc.), amino or substituted amino (e.g., dimethylamino, etc.) that is positioned either ortho (o-) or more typically para (p-) on the benzene ring.

Another group of representative ester derivatives that can be obtained by the process of the present invention are those having either of the following formulas XV or XVI:

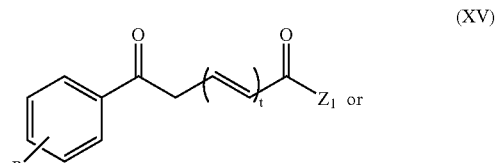

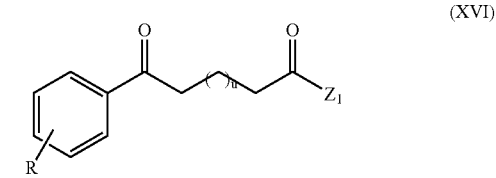

wherein $Z_1$ is defined as before and is typically —NHOH, or —CH$_2$—PO$_3$R$_{13}$R$_{15}$, wherein R$_{13}$ and R$_{15}$ are each typically hydrogen or an alkyl group having from 1 to 4 carbon atoms, more typically ethyl or methyl; t is at least 1 and is typically from 1 to 3, more typically 1 or 2; u is at least 2 and is typically from 2 to 6, more typically from 2 to 4; and R is either hydrogen or a substituent group, typically an electron donating substituent group such as halo (e.g., bromo, etc.), amino or substituted amino (e.g., dimethylamino, etc.) that is positioned either ortho (o-) or more typically para (p-) on the benzene ring.

Another group of representative ester derivatives that can be obtained by the process of the present invention are those having the following formula XVII:

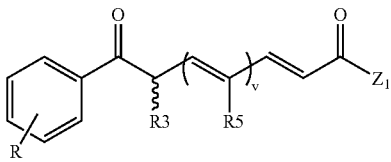

(XVII)

wherein $Z_1$ is defined as before and is typically —NHOH, or —$CH_2$—$PO_3R_{13}R_{15}$, wherein $R_{13}$ and $R_{15}$ are each typically hydrogen or an alkyl group having from 1 to 4 carbon atoms, more typically ethyl or methyl; $R_3$ an alkyl group having from 1 to 2 carbon atoms, typically methyl, $R_5$ is an alkyl group having from 1 to 4 carbon atoms, typically methyl; v is at least 1, and is typically from 1 to 2, more typically 1; and R is either hydrogen or a substituent group, typically an electron donating substituent group such as halo (e.g., bromo, etc.), amino or substituted amino (e.g., dimethylamino, etc.) that is positioned either ortho (o-) or more typically para (p-) on the benzene ring.

A particularly representative carboxylic acid or carboxylic acid derivative of formula XVII that can be obtained by the process of the present invention is trichostatic acid (R is p- or 4-dimethylamino; $R_3$ and $R_5$ are each methyl; v is 1; and $Z_1$ is —OH) or trichostatin A (R is p- or 4-dimethylamino; $R_3$ and $R_5$ are each methyl; t is 1 $Z_1$ is —NHOH). Scheme 1 of FIG. 1 illustrates an embodiment of a synthesis of trichostatic acid or trichostatin A according to the process of the present invention, starting with the N-acyl oxazolidinone compound of formula 1. See Evans, *J. Am. Chem. Soc.*, 103 (1981), p. 2127 et seq. (herein incorporated by reference), for a description of the preparation of compound 1. As shown in step 1 of Scheme 1, compound 1 is reacted with 4-(dimethylamino)benzaldehyde using, for example, triethylamine and di-n-butylboryl trifluoromethanesulfonate, to provide the respective compound 2 (typically a mixture of diasterioisomers). See Evans, *J. Am. Chem. Soc.*, supra, for a description of the preparation of compound 2. As shown in step 2 of Scheme 1, compound 2 is then reacted with methanol using trifluoroacetic acid as the catalyst to convert the hydroxy group to a methoxy group in providing the respective compound 3. As shown in step 3 of Scheme 1, compound 3 is converted to the aldehyde of formula V in either one or two steps by treatment with lithium borohydride, followed by treatment with a pyridine/sulfur trioxide complex. See Djuric, *Tetrahedron Lett.*, 29 (1988): pp. 3459–62 (herein incorporated by reference), for a description of the lithium borohydride treatment step; Parikh et al., *J. Am. Chem. Soc.*, 89 (1967): p. 5505 et seq. (herein incorporated by reference), for a description of the pyridine/sulfur trioxide treatment step. Typically, compound 3 is converted in step 3 to the aldehyde of formula V just prior to carrying out step 4 of Scheme 1.

As further illustrated in step 4 of Scheme 1 in FIG. 1, the aldehyde of formula V is combined with the reaction product of the unsaturated phosphonate ester of formula VI (typically a mixture of 2- and 3-unsaturated phosphonate esters) and lithium hexamethyldisilazide (as the weakly nucleophilic/strong base) in a solvent such as THF. The reaction temperature is gradually warmed from about −78° C. when the reagents are initially added or combined together, up to about 25° C. to provide the unsaturated ester of formula VII (typically as a 1:2 ratio cis:trans isomers) in yields of from about 60 to about 80%. In step 5 of Scheme 1, the unsaturated ester of formula VII is hydrolyzed (saponified) by treatment with lithium hydroxide to provide the respective carboxylic acid of formula VIII. See Corey, *Tetrahedron Lett.*, (1977): p. 3529 et seq. (herein incorporated by reference); K. Mori et al., "Synthetic Microbial Chemistry: Synthesis of Trichostatin-A, a Potent Differentiation Inducer of Friend Leukemic-Cells, and its Antipode," *Tetrahedron*, 44 (1988): pp. 6013–20 (herein incorporated by reference), for a general description of how to carry out hydrolysis/saponification step 5. In step 6 of Scheme 1, the carboxylic acid of formula VIII is oxidized by DDQ to form trichostatic acid (formula IX). See I. Fleming et al., "The Total Synthesis of (+/−)-Trichostatin-A—Some Observations on the Acylation and Alkylation of Silyl Enol Ethers, Silyl Dienol Ethers and a Silyl Trienol Ether," *Tetrahedron*, 39 (1983): pp. 841–46 (herein incorporated by reference), for a general description of how to carry out oxidation step 6 to obtain trichostatic acid. In step 7 of Scheme 1, trichostatic acid is reacted with a hydroxylamine (e.g., O-(2-methoxy-2-propyl)hydroxylamine) using ethyl chloroformate to provide the hydroxamic acid trichostatin A (formula X). See K. Mori et al., supra, for a general description of how to carry out step 7 to obtain trichostatin A.

Figure 2:
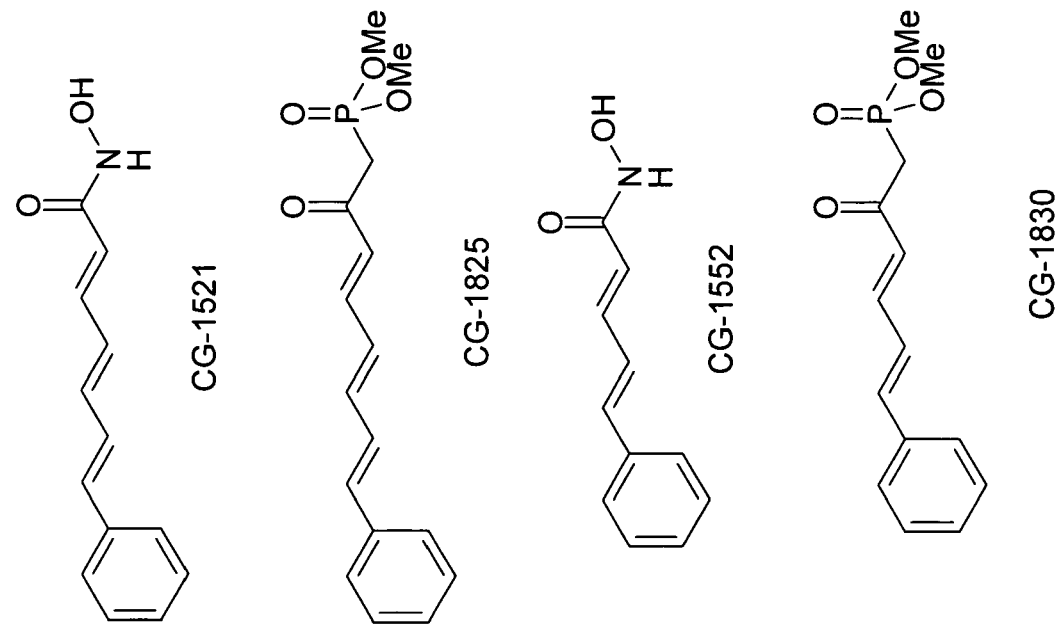
FIGS. 2 and 3 show some representative HDAC inhibitors other than trichostatin A that may be prepared by the process of the present invention.
Figure 2:
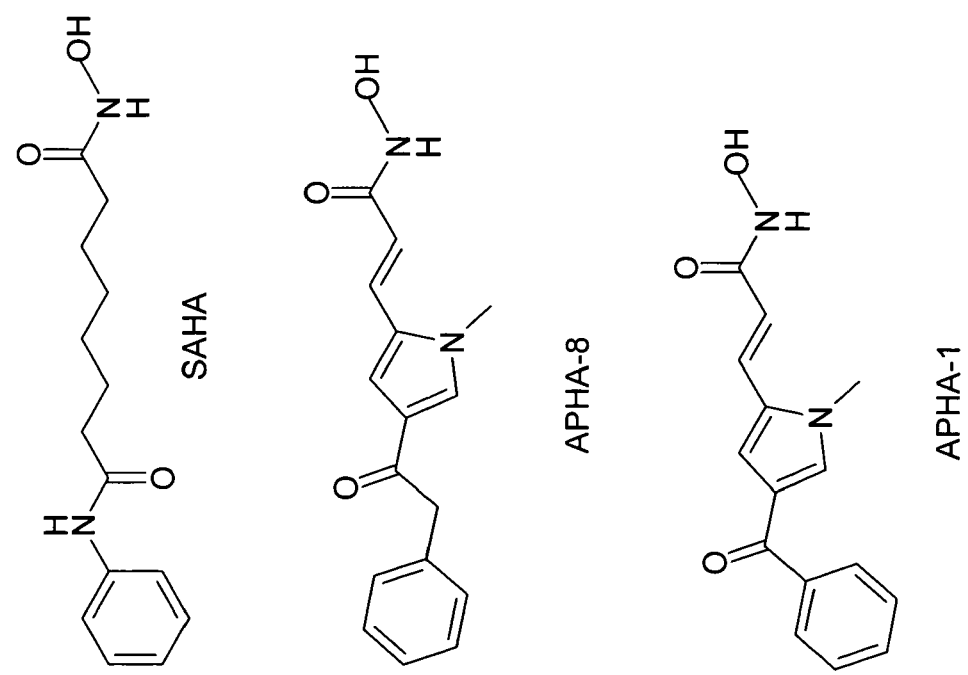
Figure 3:
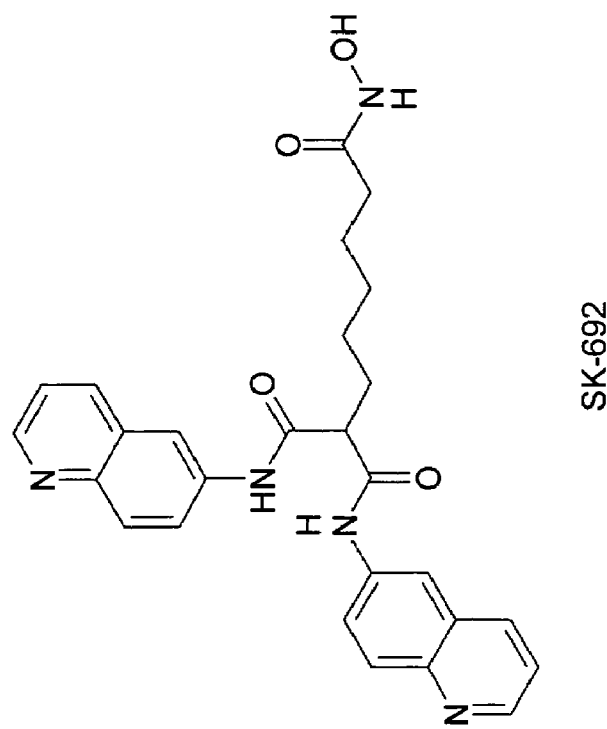
Figure 3:
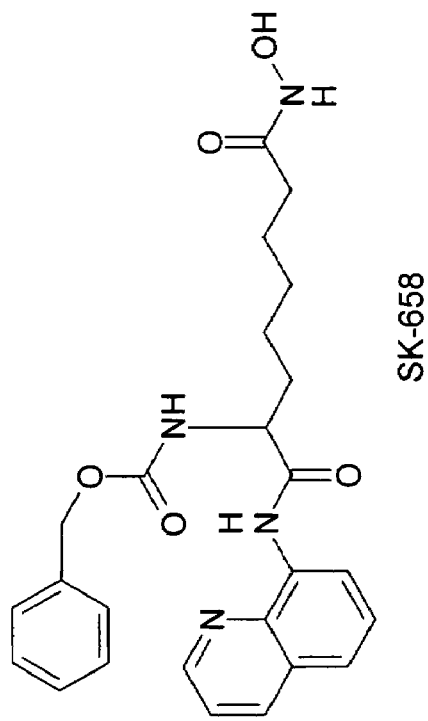
Figure 3:
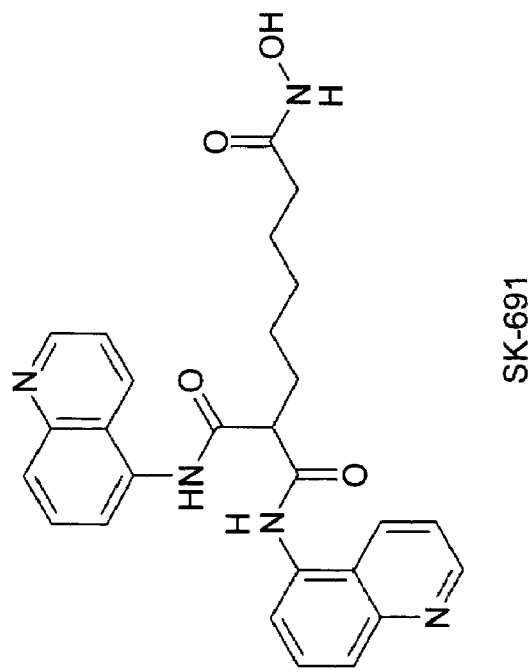

In addition to trichostatic acid and trichostatin A, the process of the present invention can be used to prepare a variety of HDAC inhibitors (e.g., carboxylic acids, hydroxamic acids, other carboxylic acid derivatives, etc.), their respective intermediates, as well as other compounds useful for other pharmacological or drug uses. Other representative HDAC inhibitors that can be prepared by the process of the present invention include those shown in FIGS. 2 and 3 and identified as suberoylanilide hydroxamic acid (SAHA), the diamide or amide-carbamate hydroxamic acids identified as SK-658, SK-692, and SK-691, the unsaturated aliphatic aromatic hydroxamic acids identified as APHA-1 and APHA-8, the unsaturated aliphatic hydroxamic acids identified as CG 1521 and CG 1552, and the unsaturated aliphatic 2-ketophosphonates identified as CG 1825, and CG 1830. See Wang et al., "On the Function of the 14 Å Long Internal Cavity of Histone Deacetylase-Like Protein: Implications for the Design of Histone Deacetylase Inhibitors," *J. Med. Chem.*, 47 (2004): pp. 3409–17, which is incorporated by reference. The process of the present invention is especially useful in preparing HDAC inhibitors, and intermediates thereof, such as trichostatic acid and trichostatin A, compounds such as CG 1521, CG 1552, CG 1825 and CG 1830, etc., that require the preservation of certain desired stereoisomeric configurations and/or have two or more double bonds directly in the carbon chain between the $R_1$ and $R_8$ groups, and in particular where the number of carbon atoms directly in this chain is from 4 to 8, more typically from 7 to 8, as well as those HDAC inhibitors, and intermediates thereof.

EXAMPLE

The following is a detailed description of the synthesis of trichostatic acid and trichostatin A according to Scheme 1 of FIG. 1:

Step 1: Synthesis of Compound 2.

Di-n-butylboryl trifluoromethanesulfonate (2.35 mL, 2.35 mmol, 1M in DCM) is added dropwise over 1 hour to a 0° C. solution of compound 1 ((S)-3-(1-oxoprop-1-yl)-4-(phenylmethyl-1,3-oxazolidin-2-one) (0.5 g, 2.14 mmol) in 2 mL of DCM. To the resulting copper colored solution is added triethylamine (0.361 mL, 2.6 mmol) over 0.5 hours. The resulting yellow solution is cooled to −78° C., a solution of 4-(dimethylamino)benzaldehyde (356 mg, 2.35 mmol) in 2 mL of dichloromethane (DCM) is then added dropwise, and the temperature is maintained at −78° C. for 20 min. This mixture is allowed to warm to 0° C., and is then stirred at 0° C. for 1 hour. The tan solution is cooled to −10° C., and the reaction is then quenched by the addition of a pH 7 phosphate buffer solution (2.15 mL). A solution of MeOH:30% aqueous $H_2O_2$ (2:1 ratio, 6.5 mL) is then added dropwise while keeping the temperature below 10° C., and the resulting mixture is then stirred at 0° C. for 1 hour. Volatiles are then removed by evaporation under vacuum, and the residue is extracted with DCM. The combined organic extracts are washed with saturated aqueous $NaHCO_3$ and brine, dried over $MgSO_4$, filtered, and the volatiles then removed by evaporation under vacuum. The residue is purified by flash chromatography (30% ethyl acetate in hexane) to provide a white solid (0.76 g, 93% yield) comprising compound 2 ((4S)-4-benzyl-3-(2S,3S)-3-[4-(dimethylamino)phenyl]-3-hydroxy-2-methylpropanoyl-1,3-oxazolan-2-one) as a 5:1 mixture of diastereomers. Analytical: IR 3514, 2919, 1779, 1695, 1523, 1384, 1351, 1209, 816, 704 cm$^{-1}$; $^1$H NMR (CDCl$_3$) 7.36–7.16 (7H, m, ArH's), 6.72–6.66 (2H, d, J=9.0 Hz, ArH's), 4.99–4.91 (1H, d, J=5.1 Hz, CHOH), 4.56–4.46 (1H, m, CHMe), 4.17–4.06 (2H, m, ½ oxazolidinone-CH$_2$+CHBn), 4.04–3.93 (1H, m, ½ oxazolidinone-CH$_2$—), 3.27–3.19+2.79–2.70 (2H, ABX, J=3.0, 13.5, 9.0, 151.8, PhCH$_2$), 2.92 (6H, s, NMe$_2$), 1.30–1.26 (3H, d, J=6.9 Hz, CHMe); $^{13}$C NMR (CDCl$_3$) δ 176.77, 153.24, 150.36, 135.45, 129.72, 129.65, 127.64, 127.57, 127.31, 112.61, 74.55, 66.34, 55.61, 44.99, 40.96, 38.04, 12.02; m/z (+ve-FAB) 382 (M+H); HRMS for $C_{22}H_{26}N_2O_4$+H calcd 382.1893, found 382.1884.

Step 2: Synthesis of Compound 3.

To a solution of compound 2 from step 1 (2.5 g, 6.5 mmol) in MeOH (250 mL) is dropwise added trifluoroacetic acid until the pH of the mixture reaches 3 to 4. The mixture is then stirred overnight at room temperature. Saturated aqueous NaHCO$_3$ (50 mL) is then added, the solvent is removed by evaporation under vacuum, and the residue is purified by flash chromatography to provide a white solid (2.0 g, 80% yield) comprising compound 3 ((4S)-4-benzyl-3-(2S,3R/S)-3-[4-(dimethylamino)phenyl]-3-methoxy-2-methylpropanoyl-1,3-oxazolan-2-one) as a 4:1 mixture of diastereomers. Analytical: IR 2980, 2933, 2881, 1781, 1698, 1614, 1523, 1384, 1350, 1210, 1096, 819, 704 cm$^{-1}$; $^1$H NMR (CDCl$_3$) δ (major isomer) 7.38–7.14 (7H, m, ArH's), 6.76–6.70 (2H, d, J=8.7 Hz, ArH's), 4.82–4.72 (1H, m, CHOMe), 4.30–4.15 (4H, m, CH's), 3.35–3.27+2.86–2.76 (2H, ABX, J=147.3, 13.8, 9.6, 2.7 Hz, CH$_2$Ph), 3.10 (3H, s, OMe), 2.98 (6H, s, NMe$_2$), 0.98–0.91 (3H, d, J=6.6 Hz, CHME); $^{13}$C NMR (CDCl$_3$) δ 176.41, 153.53, 150.75, 135.73, 129.77, 129.17, 129.13, 128.57, 127.51, 112.48, 86.05, 66.30, 56.65, 55.81, 44.31, 40.81, 38.25, 14.85; m/z (+ve-FAB) 396 (M$^+$); HRMS for $C_{23}H_{28}N_2O_4$ calcd 396.2049, found 396.2044.

Step 3: Providing Aldehyde of Formula V.

A solution of compound 3 from step 2 (300 mg, 0.75 mmol) in THF (1 mL) is cooled to 0° C. Methanol (0.053 mL) and LiBH$_4$ (1.125 mL, 2.25 mmol, 2 M in THF) are added sequentially and the mixture is then stirred at room temperature overnight. The reaction is then quenched by the addition of a 0.5 M solution of Rochelle's salt (2 mL), diluted with ether (2 mL) and then stirred vigorously for 2 hours. The mixture is then separated and extracted further with ether. The combined organic extracts are washed with brine, dried over sodium sulfate, filtered, and the solvent then removed by distillation under vacuum. Purification by column chromatography provides a clear oil (129 mg, 77% yield) comprising a mixture of isomers of the respective alcohol (2R,3R/S)-3-[4-(dimethylamino)phenyl]-3-methoxy-2-methylpropan-1-ol). Analytical: $^1$H NMR (CDCl$_3$) δ (major isomer) 7.18–7.10+6.76–6.67 (4H, AB, J=8.7 Hz, ArH's), 3.92–3.84 (1H, d, J=9.3 Hz, CHOMe), 3.70–3.62 (2H, m, CH$_2$OH), 3.15 (3H, s, OMe), 2.96 (6H, s, NMe$_2$), 2.12–2.00 (1H, m, CHMe), 0.65–0.59 (3H, d, J=6.9 Hz, CH Me); $^{13}$C NMR (CDCl$_3$) δ (major isomer) 150.52, 128.62, 128.40, 128.13, 112.45, 90.98, 68.77, 56.37, 41.98, 40.82, 14.17. To a solution of this alcohol (200 mg, 0.90 mmol) and triethylamine (0.80 mL, 5.65 mmol) in dry DMSO (1.9 mL) is added a pyridine-sulfur trioxide complex (429 mg, 2.7 mmol) in DMSO (1.9 mL). After the addition of the pyridine-sulfur trioxide complex, the solution is stirred at room temperature for 15 min., poured onto an ice/water mixture, and then extracted with ether. The ether layers are washed with water and then brine, dried over sodium sulfate, filtered, and the solvent then removed by distillation under vacuum (at a temperature below 40° C.). After being left under high vacuum for 2 hours, a product is obtained (in >99% yield) comprising the aldehyde of formula V.

Step 4: Synthesis of Unsaturated Ester (Formula VII).

a. Synthesis of Phosphonate Esters (Formula VI).

To a solution of (E)-4-bromo-2-pentenoic acid (5 g, 28 mmol) in methanol (250 mL) is added a catalytic amount of sulfuric acid. The mixture is stirred at room temperature for 24 hours. Saturated aqueous NaHCO$_3$ (50 mL) is added, and methanol is then removed by distillation under vacuum. The resulting residue is extracted with ether, and the organic layers are then combined, washed with brine, dried over MgSO$_4$, filtered, and the solvent then removed by distillation under vacuum to yield a product (80%) comprising methyl (E)-4-bromo-2-pentenoate. This methyl ester (1 g, 5.2 mmol) is heated to 120° C., triethyl phosphite (0.99 mL, 5.6 mmol) is then added dropwise over a 1 hour period, and the mixture held at 120° C. for 24 to 36 hours (while being monitored using NMR samples). The resulting crude mixture is purified by chromatography (using 70% ethyl acetate in hexane), and then distilled to provide a clear oil (0.468 g, 36% yield) comprising a 1:1 mixture of the unsaturated phosphonate ester isomers of formula VI (methyl (E)-4-(diethoxyphosphoryl)-2-pentenoate and methyl (E)-4-(diethoxyphosphoryl)-3-pentenoate). Analytical: IR 2984, 1739 (d), 1648, 1438, 1250, 1052, 1023, 965, 791 cm$^{-1}$; $^1$H NMR (CDCl$_3$) δ (both isomers) 7.02–6.88 (0.5H, m), 6.75–6.57 (0.5H, dtt, J=23.1, 14.1, 3.3 Hz), 5.96–5.86 (0.5H, ddt, J=18.6, 4.8, 1.5 Hz), 4.15–3.99 (4H, m, OEt), 3.74–3.71 (1.5H, d, J=1.2 Hz, OMe), 3.70–3.67 (1.5H, d. J=1.5 Hz, OMe), 3.25–3.15 (1H, m), 2.70–2.90 (0.5H, m), 1.85–1.76

(0.5H, d, J=14.4 Hz), 1.39–1.26 (4.5H, m); m/z (+veFAB) 251 (M+H+); HRMS for $C_{10}H_{19}O_5P$+H calcd 251.1048, found 251.1045.

b. Reacting Aldehyde (Formula V) with Phosphonate Esters (Formula VI).

To a solution of the mixed unsaturated phosphonate esters of formula VI from step 4a (0.27 g, 1.08 mmol) in THF (4 mL) at –78° C. is added dropwise LiHMDS (1.17 mL, 1.17 mmol, 1M solution in THF). The reaction mixture is stirred at –78° C. for 30 min., warmed to –40° C. over 1 hour, and then cooled back down to –78° C. A solution of the aldehyde of formula V from step 3 in THF (4 mL) is then added to this reaction mixture, and the resulting combined reaction mixture is allowed to reach room temperature while being stirred and left for 24 hours. The stirred mixture is then cooled to 0° C., quenched with saturated aqueous $NH_4Cl$, and then stirred for 0.5 hours. This stirred mixture is then extracted with ether, and the combined organic layers are washed with brine, dried over sodium sulfate, filtered, and the solvent then removed by distillation under vacuum. The vacuum distilled mixture is purified by flash chromatography to provide a yellow oil (223 mg, 78% yield) comprising the unsaturated ester of formula VII ((2E,4E,6R)-7-[4-(dimethylamino)phenyl]-7-methoxy-4,6-dimethyl-2,4-heptadienoate) as a 2:1 mixture of trans:cis isomers. Analytical: $^1H$ NMR ($CDCl_3$) δ (trans) 7.44–7.35 (1H, d, J=15.6 Hz, —CH=CHCO$_2$Me), 7.18–7.10+6.77–6.70 (4H, AB, J=8.4 Hz, ArH's), 5.92–5.85 (1H, d, J=9.6 Hz, —CH=CMe—), 5.84–5.76 (1H, d, J=15.6 Hz, =CHCO$_2$Me), 3.92–3.88 (1H, d, J=6.9 Hz, CHOMe), 3.78 (3H, S, CO$_2$Me), 3.17 (3H, s, OMe), 2.98 (6H, s, NMe$_2$), 2.98–2.82 (1H, m, MeOCHCH(Me)CH=), 1.73 (3H, s, =CH(Me)CH=), 0.89–0.85 (3H, d, J=6.6 Hz, CHMe); (cis isomer key differences) 7.72–7.62 (1H, d, J=15.6 Hz, —CH=CHCO$_2$Me), 5.92–5.82 (1H, d, J=15.6 Hz, =CHCO$_2$Me), 5.75–5.68 (1H, d, J=9.9 Hz, —CH=CMe—), 3.90–3.85 (1H, d, J undeterminable, CHOMe), 3.78 (3H, S, CO2Me), 1.89 (3H, s, =CH(Me)CH=); m/z (+ve FAB) 318 (M+H); HRMS for $C_{19}H_{27}NO_3$+H calcd 318.2069, found 318.2047.

Step 5: Saponification of Unsaturated Ester (Formula VII) to Carboxylic Acid (Formula VIII).

The unsaturated ester of formula VII obtained in step 5 is saponified with LiOH according to the procedure described in K. Mori et al, "Synthetic Microbial Chemistry: Synthesis of Trichostatin-A, a Potent Differentiation Inducer of Friend Leukemic-Cells, and its Antipode," Tetrahedron, 44 (1988): pp. 6013–20. Work up utilizes phosphate buffer solutions (pH 7 and 4) for an easier extraction and then column chromatography to provide a purified product (90% yield) comprising the carboxylic acid of formula VIII ((2E,4E,6R)-7-[4-(Dimethylamino)phenyl]-7-methoxy-4,6-dimethyl-2,4-heptadienoic acid). Analytical: $^1H$ NMR ($CDCl_3$) δ (major isomer) 7.49–7.41 (1H, d, J=15.6 Hz, C—CH=CHCO$_2$Me), 7.15–7.08+6.68–6.76 (4H, AB, J=9 Hz, ArH), 5.97–5.89 (1H, d, J=9.3 Hz, —CH=CMe—), 5.74–5.83 (1H, d, J=15.9 Hz, =CHCO$_2$Me), 3.85–3.92 (1H, d, J=6.9 Hz, CHOMe), 3.16 (3H, s, OMe), 2.97 (6H, s, NMe$_2$), 1.73 (3H, s, =C(Me)—CH=), 0.83–0.90 (3H, d, J=6.9 Hz, —CH(Me)—).

Step 6: Synthesis of Trichostatic Acid (Formula IX).

To a stirred solution of the carboxylic acid of formula IX from step 5 (77 mg, 0.25 mmol) in DCM (1.15 mL) containing water (250 μl) is added solid 2,3-dichloro-4,5-dicyanoquinone (DDQ) (63 mg, 0.27 mmol) at room temperature. The resulting mixture is stirred for 30 min. and is then filtered through Celite. The retained solid is washed further with DCM, the combined filtrates are dried over sodium sulfate, and the solvent then removed by distillation under vacuum. The resulting crude product is vacuum distilled and is then purified by flash chromatography using a solvent gradient starting with a 1.5:98.5 mixture of isopropanol:benzene and increasing to a 4:96 mixture of isopropanol:benzene to provide a product (68 mg, 95% yield) comprising trichostatic acid of formula IX ((2E,4E, 6R)-7-[4-(dimethylamino)phenyl]-4,6-dimethyl-7-oxo-2,4-heptadienoic acid) as the major component for which spectroscopic data are obtained that corresponds to the known spectroscopic data for trichostatic acid.

Step 7: Synthesis of Trichostatin A (Formula X).

The trichostatic acid from step 6 is reacted with O-(2-methoxy-2-propyl)hydroxylamine using ethyl chloroformate according to the procedure described in K. Mori et al, "Synthetic Microbial Chemistry: Synthesis of Trichostatin-A, a Potent Differentiation Inducer of Friend Leukemic-Cells, and its Antipode," Tetrahedron, 44 (1988): pp. 6013–20 (herein incorporated by reference), to provide trichostatin A (formula X).

All documents, patents, journal articles and other materials cited in the present application are hereby incorporated by reference.

Although the present invention has been fully described in conjunction with several embodiments thereof with reference to the accompanying drawings, it is to be understood that various changes and modifications may be apparent to those skilled in the art. Such changes and modifications are to be understood as included within the scope of the present invention as defined by the appended claims, unless they depart therefrom.

What is claimed is:

1. A process for preparing trichostatic acid or trichostatin A comprising the following steps:

(a) providing an aldehyde having the following formula V:

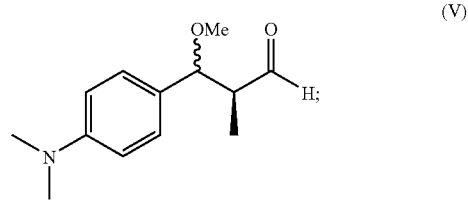

(b) providing an unsaturated phosphonate ester having the following formula VI:

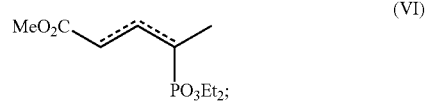

(c) reacting the aldehyde of formula V with the phosphonate ester of formula VI to provide an unsaturated ester having the following formula VIII:

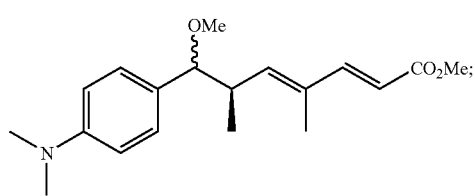

(VII)

(d) hydrolyzing the unsaturated ester of formula VII to provide a carboxylic acid having the following formula VIII:

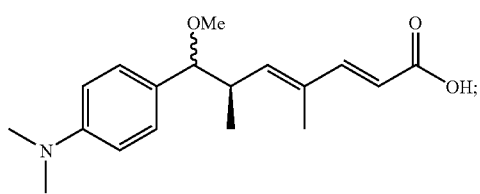

(VIII)

(e) converting the carboxylic acid of formula VIII to trichostatic acid; and (f) optionally converting the trichostatic acid of step (e) to trichostatin A.

2. The process of claim 1 wherein the aldehyde of formula V is prepared by the following steps:

(1) providing compound 1 having the following formula:

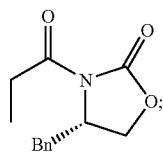

(1)

(2) reacting compound 1 with 4-(dimethylamino)benzaldehyde to provide compound 2 having the following formula:

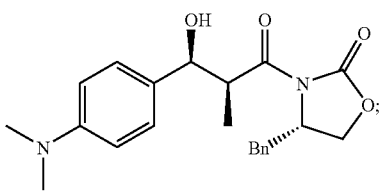

(2)

(3) reacting compound 2 with methanol to provide compound 3 having the following formula:

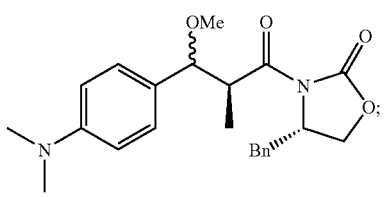

(3)

and (4) converting compound 3 to the aldehyde of formula V.

3. The process of claim 1, wherein step (c) is carried out by adding a strong base that is weakly nucleophilic to the phosphonate ester of formula VI before reacting with the aldehyde of formula V.

4. The process of claim 3, wherein the strong base is lithium hexamethyldisilazide, lithium amide, lithium di-isopropyl amide, lithium isopropylcyclohexyl amide, lithium dicyclohexylamide, sodium hexamethyldisilazide, or potassium hexamethyldisilazide.

5. The process of claim 4, wherein the strong base is lithium hexamethyldisilazide.

6. The process of claim 1, wherein step (e) is carried by oxidizing the carboxylic acid of formula VIII with 2,3-dichloro-5,6-dicyanobenzoquinone.

7. The process of claim 1, wherein step (f) is carried out by reacting O-(2-methoxy-2-propyl)hydroxylamine with trichostatic acid to provide trichostatin A.

8. The process of claim 7, wherein step (f) is carried out in the presence of ethyl chloroformate.

9. The process of claim 1, wherein step (f) is carried out by reacting a hydroxylamine with trichostatic acid to provide trichostatin A.

10. The process of claim 9, wherein step (f) is carried out in the presence of ethyl chloroformate.

11. The process of claim 1, wherein step (e) is carried out by treatment of the carboxylic acid of formula VIII with a selective oxidizing agent.

12. The process of claim 11, wherein the selective oxidizing agent comprises 2,3-dichloro-5,6-dicyanobenzoquinone.

13. The process of claim 2, wherein step (4) is carried out by treating compound 3 with lithium borohydride, followed by treatment with a pyridine-sulfur trioxide complex.

* * * * *